US005582746A

United States Patent [19]

Barbee et al.

[11] Patent Number: 5,582,746

[45] Date of Patent: *Dec. 10, 1996

[54] REAL TIME MEASUREMENT OF ETCH RATE DURING A CHEMICAL ETCHING PROCESS

[75] Inventors: Steven G. Barbee, Dover Plains; Tony F. Heinz, Chappaqua, both of N.Y.; Yiping Hsiao, San Jose, Calif.; Leping Li, Poughkeepsie; Eugene H. Ratzlaff, Hopewell Junction, both of N.Y.; Justin W. Wong, Burlington, Vt.

[73] Assignee: International Business Machines Corporation, Armonk, N.Y.

[*] Notice: The term of this patent shall not extend beyond the expiration date of Pat. No. 5,338,390.

[21] Appl. No.: 269,862

[22] Filed: Jun. 30, 1994

Related U.S. Application Data

[63] Continuation-in-part of Ser. No. 985,413, Dec. 4, 1992, Pat. No. 5,338,390.

[51] Int. Cl.$^6$ ................................................. H01L 21/306
[52] U.S. Cl. .............................................. 216/86; 156/627.1
[58] Field of Search ...................... 216/86, 84; 156/627.1; 204/129.2, 129.5

[56] References Cited

U.S. PATENT DOCUMENTS

| 2,933,675 | 4/1960 | Hoelzle ................................... 324/30 |
| 3,163,568 | 2/1961 | Mieux .................................... 156/627 |
| 3,553,052 | 1/1971 | Jubb, Jr. ................................ 156/345 |
| 3,874,959 | 4/1975 | Hoekstra ................................. 156/7 |
| 3,959,046 | 5/1976 | Bussmann et al. ....................... 156/7 |
| 3,964,956 | 6/1976 | Snyder ................................... 156/345 |

(List continued on next page.)

FOREIGN PATENT DOCUMENTS

| 55-46568 | 4/1980 | Japan . |
| 59-52838 | 3/1984 | Japan ..................................... 156/627 |
| 59-113626 | 6/1984 | Japan ..................................... 156/627 |
| 273634 | 3/1990 | Japan ..................................... 156/627 |
| 496346 | 3/1992 | Japan . |
| 8100646 | 3/1981 | WIPO ..................................... 156/62 |

OTHER PUBLICATIONS

Goubau, W. M., "Capacitive Etch Rate Monitor for Dielectric Etching", IBM Technical Disc. Bulletin vol. 31, No. 1, Jun. 1988, 448–449.

Liu et al., "Resistance/Capacitance Methods for Determining Oxide Etch End Point", IBM Technical Disc. Bulletin vol. 16, No. 8, Jan. 1974, 2706–2707.

Hoekstra, J.P., "Establishing End Point During Delineation Process", IBM Technical Disc. Bulletin vol. 16, No. 6, Nov. 1973, 1717–1720.

Bassous et al., "An In–Situ Etch Rate Monitor Controller", IBM Technical Disc. Bulletin vol. 20, No. 3, Aug. 1977, 1232–1234.

*Primary Examiner*—R. Bruce Breneman
*Assistant Examiner*—Mara Ronda
*Attorney, Agent, or Firm*—Steven J. Soucar; Dale M. Crockatt

[57] ABSTRACT

A contactless method and apparatus for real-time in-situ monitoring of a chemical etching process during etching of at least one wafer in a wet chemical etchant bath are disclosed. The method comprises the steps of providing two conductive electrodes in the wet chemical bath, wherein the two electrodes are proximate to but not in contact with a wafer; monitoring an electrical characteristic between the two electrodes as a function of time in the etchant bath of the at least one wafer, wherein a prescribed change in the electrical characteristic is indicative of a prescribed condition of the etching process; and recording a plurality of values of the electrical characteristic as a function of time during etching. From the plurality of recorded values and corresponding times, instantaneous etch rates, average etch rates, and etching end points may be determined. Such a method and the apparatus therefor are particularly useful in a wet chemical etch station.

11 Claims, 1 Drawing Sheet

U.S. PATENT DOCUMENTS

| | | | |
|---|---|---|---|
| 4,220,508 | 9/1980 | Kotani et al. | 204/129.65 |
| 4,338,157 | 7/1982 | Kanda | 156/627 |
| 4,497,699 | 2/1985 | de Wit et al. | 204/129.2 |
| 4,621,037 | 11/1986 | Kanda et al. | 430/30 |
| 4,755,442 | 7/1988 | Hasebe et al. | 156/627 |
| 4,793,895 | 12/1988 | Kaanta et al. | 156/627 |
| 4,969,973 | 11/1990 | Rinck et al. | 156/627 |
| 4,989,157 | 1/1991 | Balisky | 364/500 |
| 4,995,939 | 2/1991 | Ferenczi et al. | 156/627 |
| 5,071,508 | 12/1991 | Scheithauer | 156/627 |
| 5,081,421 | 1/1992 | Miller et al. | 324/671 |
| 5,198,072 | 3/1993 | Gabriel et al. | 156/627 |
| 5,338,390 | 8/1994 | Barbee et al. | 216/86 |

REAL TIME MEASUREMENT OF ETCH RATE DURING A CHEMICAL ETCHING PROCESS

CROSS-REFERENCE TO RELATED APPLICATION

This is a continuation-in-part of U.S. patent application Ser. No. 985,413, filed on Dec. 4, 1992, which issued as U.S. Pat. No. 5,338,390 on Aug. 16, 1994.

BACKGROUND OF THE INVENTION

1. Field of the Invention

The present invention generally relates to a method and apparatus for monitoring the etching condition of a chemical etching process, and more particularly, to an improved contactless real-time in-situ method and apparatus for the same.

2. Discussion of the Related Art

Etching rates and etch end points must be carefully monitored and controlled in order to end etching processes at the desired time. In semiconductor processing, inadequate or excess etching time can result in undesirable film patterning. For instance, for semiconductor devices having film layers or features in the micron and sub-micron range, an inadequate etch or an excess etch would result in the insufficient removal or the excess removal of a desired layer. Insufficient removal of a desired layer can result in an undesired electrical open or electrical short when the desired layer to be removed is an insulator or a conductor, respectively. Additionally, if the etch is in excess, undercutting or punch through can occur resulting in poorly defined film patterning or total lift-off. Inadequate or excess etching time further leads to undesirable reliability problems in the subsequently fabricated semiconductor device. As a semiconductor wafer is extremely expensive due to many processing steps involved in the making thereof, the need to critically control the etching end point in an etching process is highly desirable.

An etch end point must be accurately predicted and/or detected to terminate etching abruptly. Etch rates, etch times, and etch end points are difficult to consistently predict due to lot-to-lot variations in film thickness and constitution, as well as etch bath temperature, flow, and concentration variability. That is, an etch rate is dependent upon a number of factors, which include, etchant concentration, etchant temperature, film thickness, and the film characteristics. Non-uniformity can result from differences across the wafer in film thickness, or can result from differences in the physical or chemical properties of the film such as stoichiometry, density, or intrinsic stress. Precise control of any of these factors can be very expensive to implement, for example, concentration control. However, substantial overetching to remove all slower etching material can lead to wafer yield loss and the decreased reliability of the resulting electronic devices. In addition, circuit dimensions must be made larger to allow for overetch tolerances. Thus, a high degree of control of the etching process is desirable in the manufacture of semiconductor devices.

Currently, most etch rate end point determination techniques depend on indirect measurement and estimation techniques. Some etch monitoring techniques have relied on external measurements of film thickness followed by etch rate estimation and an extrapolated etch end point prediction. However, imprecision is introduced into the estimation of an etch process unless the basis for extrapolation is representative of etching characteristics near the etching end point. Where etch rates may vary due to batch-to-batch differences in the chemical and physical characteristics of the film or the etchant, these extrapolation methods are inadequate. Interrupted measurement techniques are also imprecise where the etch rate is not linear, such as where an induction period occurs at the beginning of the etch, where the instantaneous etch rate varies within the film, or where the removal of material from a partially etched film occurs after removal of the wafer from the etchant bath but prior to rinsing.

Previous methods for measuring film etching uniformity include optical techniques such as ellipsometry, reflectance spectroscopy, and the prism coupler method, on blanket films on monitor wafers. Film etch characteristics measured on monitor wafers may not be representative of product wafer etch characteristics. Yet other techniques monitor the etch rate of a fiducial region of the product wafer and require optical access to the wafer in the wet etch bath. However, in-situ measurements on fiducial sites of product wafers do not always correlate to the actual film etching characteristics in the region of interest (e.g. in contact holes, on stacks of films, etc.) in the device. These measurements are spatially discrete. Furthermore, such methods are expensive as portions of the wafer are occupied by non-product fiducial areas or require additional test wafers. Such optical methods are also subject to uncertainty resulting from turbidity of the etch bath and other optical effects and uncertainty resulting from non uniform films. Such optical methods are subject to imprecision in the resulting estimate of overetch when the number of measured sites is insufficient or when the sections are not representative of the whole. Finally, optical measurements require expensive equipment and specialized training for unambiguous interpretation of results. They usually assume refractive index dispersion relations and optical constants of underlying films and substrates, which may be invalid. In addition, these techniques have limitations in the film thickness ranges for which they are applicable.

Still other techniques require physical contact of electrical leads with the wafer being etched and electrical isolation of those leads and associated areas of the wafer from the etchant. This presents problems associated with contamination, contact reliability and reproducibility, and the physical constraints which affect ease of use in manufacturing or automation.

It would thus be desirable to provide an improved method and apparatus which provides non-contact, real-time, in-situ monitoring of an etching condition of a wafer being etched.

SUMMARY OF THE INVENTION

An object of the present invention is to overcome the problems in the art discussed above.

Another object of the present invention is to provide an improved non-contact method of monitoring the etching condition of a wafer being etched.

Yet another object of the present invention is to provide an accurate real-time, in-situ method and apparatus for monitoring an etching condition of a wafer being etched.

Yet another object of the present invention is to provide an accurate real-time, in-situ method and apparatus for controlling a wafer etching process.

According to the present invention, a contactless method for real-time in-situ monitoring of a chemical etching process for the etching of at least one wafer in a wet chemical etchant bath comprises the steps of:

a) providing two conductive electrodes in the wet chemical bath, wherein said two electrodes are proximate to but not in contact with the at least one wafer;

b) monitoring an electrical characteristic between the two electrodes as a function of time in the etchant bath of the at least one wafer, wherein a prescribed change in the electrical characteristic is indicative of a prescribed condition of the etching process; and c) recording a plurality of values of said electrical characteristic as a function of time during etching.

The method of may additional comprise, any one or more of the steps of determining an instantaneous etch rate in real time from at least two of the recorded plurality of values, determining an average etch rate in real time from at least two of the recorded plurality of values, or determining an etching end point in real time from at least two of the recorded plurality of values.

In addition, according to the present invention, a contactless real-time in-situ chemical etch monitor for providing an indication of a prescribed condition of an etching process of at least one wafer to be etched in a wet chemical etchant bath comprises a means for accomplishing each of the aforesaid process steps.

BRIEF DESCRIPTION OF THE DRAWINGS

The foregoing and other teachings and advantages of the present invention will become more apparent upon a detailed description of the best mode for carrying out the invention as rendered below. In the description to follow, reference will be made to the accompanying drawing, in which.

DETAILED DESCRIPTION OF THE PREFERRED EMBODIMENTS

Figure 1:
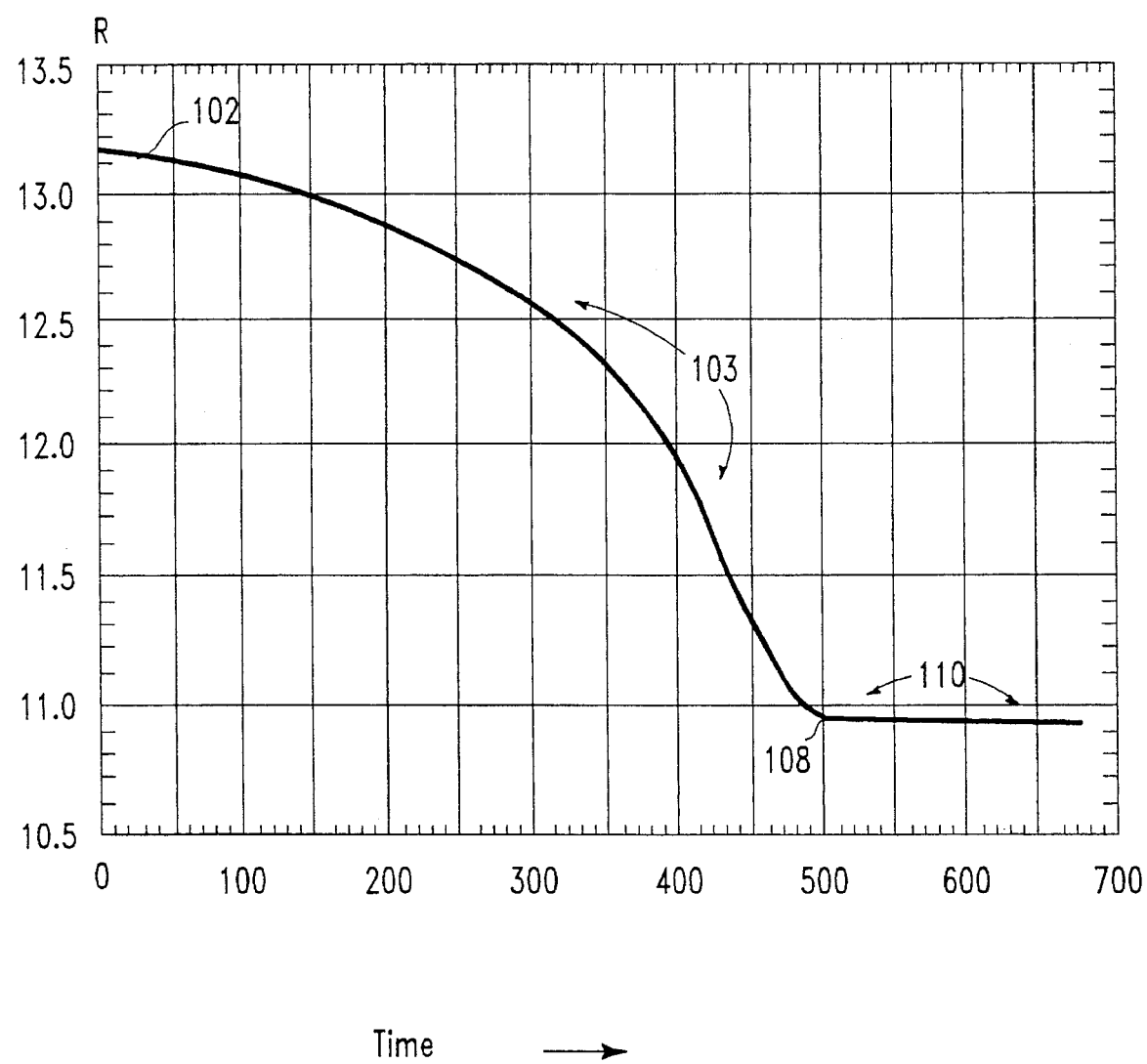
FIG. 1 shows a graph of monitored electrical characteristics according to the present invention.

Copending U.S. patent application Ser. No. 07/985,413, filed Dec. 4, 1992, entitled "Contactless Real-time In-Situ Monitoring of a Chemical Etching Process," now U.S. Pat. No. 5,338,390 assigned to the assignee of the present invention (attorney docket FI9-92-152, hereafter "'390 Patent"), the disclosure of which is hereby incorporated by reference into the present application, describes a related method and apparatus for the contactless, real-time, in-situ monitoring of a chemical etching process during etching of a wafer in a wet chemical etchant bath, wherein the two conductive electrodes are proximate to but not in contact with the at least one wafer, and further wherein said two electrodes are positioned on opposite sides of the wafer. Six copending U.S. patent applications, filed on even date herewith, entitled variously "MINIMIZING OVERETCH DURING A CHEMICAL ETCHING PROCESS", "MEASURING FILM ETCHING UNIFORMITY DURING A CHEMICAL ETCHING PROCESS", "CONTACTLESS REAL-TIME IN-SITU MONITORING OF A CHEMICAL ETCHING PROCESS", "METHOD AND APPARATUS FOR CONTACTLESS REAL-TIME IN-SITU MONITORING OF A CHEMICAL ETCHING PROCESS", "FIXTURE FOR IN-SITU NON-CONTACT MONITORING OF WET CHEMICAL ETCHING WITH PASSIVE WAFER RESTRAINT", and "METHOD AND APPARATUS FOR CONTACTLESS REAL-TIME IN-SITU MONITORING OF A CHEMICAL ETCHING PROCESS", assigned to the assignee of the present invention (attorney docket numbers FI9-93-035, FI9-93-037, FI9-93-038, FI9-94-053, FI9-94-054, and FI9-94-055 respectively), describe improvements to the method and apparatus for contactless, real-time, in-situ monitoring of chemical etching disclosed in the '390 patent. The disclosure of the aforesaid six copending applications is also hereby incorporated by reference into the present application.

The apparatus of the copending '390 application may be adapted to the present invention by including a means for recording a plurality of values of the electrical characteristic being monitored as a function of time during etching. Such values correspond to a typical output signal from the electrical characteristic analyzer such as an impedance analyzer described in the '390 patent. Monitoring of the prescribed etching characteristic is effected by electrically sensing, in-situ, changes in an electrical characteristic of the wafer, such as, the impedance or an element or elements of impedance (e.g., admittance, capacitance, inductance, reactance and/or resistance), between the two electrodes. For example, the real and imaginary parts of the impedance as a function of time may be measured.

Referring now to FIG. 1, there is shown a graphical representation as a function of time of a typical output signal from the electrical characteristic analyzer described above. More particularly, FIG. 1, represents measured resistance as a function of etch time, as disclosed in the copending '390 patent. Starting point 102 corresponds to the start of the etching process. Region 103 of the curve corresponds to thinning of the film during the etch process. Point 108 corresponds approximately to a point in time at which all features are etched to nominal size in an essentially uniform film. Region 110 of the curve corresponds to the period during which more than the nominal or desired amount of material to be removed by etching is being removed from the substrate, for example, by an undercutting process.

In the case where the film is homogeneous with respect to etching characteristics, that is, has a linear etch rate per unit of thickness at all points on the wafer, the average etch rate is determined from the time period between starting point 102 and point 108 together with a known film thickness. From any two recorded values, the average etch rate may be determined for the corresponding period. From any two recorded values which are close in time, the instantaneous etch rate may be determined.

It should be understood that the invention contemplates that the shape of the curve shown in FIG. 1 may deviate from that shown in the figure, provided that the electrical characteristic is recorded as a function of time. Based on the curve shape between any two or more points, the extent of etching uniformity of the film can be immediately discerned. This results in an etch record which is essentially a monolayer-by-monolayer etch rate depth profile of the thin film strata. Any change in the ongoing etch rate is observed as a change in the curve shape. Thus, any significant batch-to-batch variation in the homogeneity of a film that would affect the etch rate will be reflected in the batch-to-batch reproducibility of the etch records. For example, a temporary or intermittent pressure or electrical fluctuation in a film deposition process could result in transient density or stoichiometry changes in the resulting film. Alternatively, where thickness can be shown to be extremely uniform, the nonuniformity may be attributed to other physical or chemical phenomena. The monitored electrical characteristic information is not from a series of discrete measurements across the film, as in optical approaches, but is from a single measurement representative of the whole wafer. Instantaneous changes in the electrical characteristic would appear as small spikes or plateaus in the etch record, and the determined instantaneous etch rate reflects such changes.

Thus, the etching end point can be precisely determined for a product wafer. Alternatively, the etching end point may be predicted in real time by rapid analysis of the recorded values and extrapolation to the endpoint, which extrapolation is preferred to be accomplished near the end of the etching process.

With respect to the instant apparatus, the means for recording a plurality of values of the electrical characteristic being monitored as a function of time during etching receives the output signal from the analyzer. Said means include, without limitation, electrical signal storage devices, computers, and programmable controllers which are well known in the art.

In alternative embodiments, the apparatus additionally comprises any one or more of a means for determining an instantaneous etch rate in real time from at least two of the recorded plurality of values, a means for determining an average etch rate in real time from at least two of the recorded plurality of values, or a means for determining an etching end point in real time from at least two of the recorded plurality of values. Such means include, without limitation, signal analyzers, computers, and programmable controllers which are well known in the art, and which may be separate from, or part of, electrical characteristic monitoring device.

In yet another alternative embodiment, the apparatus of the present invention may comprise a means such as a computer or a programmable controller which is responsive to the end point determining means, the average etch rate determining means, or the instantaneous etch rate determining means, and which means may, in turn, control the etch process such as by actuating a wafer handling means. Furthermore, electrical characteristic monitoring device can likewise comprise an impedance analyzer and a computer or a programmable controller, the computer or programmable controller providing feedback control to initiate, control, and terminate an etching operation. Impedance analyzers, computers, and programmable controllers are well known in the art.

Finally, it is noted that many of the disclosed means may be assembled as discrete elements or together in a combined element without affecting the essential function thereof.

Thus there has been shown an improved real-time in-situ monitoring method and apparatus which provide accurate, noncontact, monitoring of an etching characteristic of an etching process. Such a method and apparatus are inexpensive to implement and ensure the integrity of the etched wafer or wafers. Etching of a wafer can be controlled precisely.

While the invention has been particularly shown and described with reference to specific embodiments thereof, it will be understood by those skilled in the art that various changes in form and detail may be made thereto, and that other embodiments of the present invention beyond embodiments specifically described herein may be made or practiced without departing from the spirit of the invention. System condition parameters, such as impedance analyzer frequency, etc., may need to be adjusted accordingly to obtain optimum detection sensitivity. Similarly, other changes, combinations and modifications of the presently disclosed embodiments will also become apparent. The embodiments disclosed and the details thereof are intended to teach the practice of the invention and are intended to be illustrative and not limiting. Accordingly, such apparent but undisclosed embodiments, changes, combinations, and modifications are considered to be within the spirit and scope of the present invention as limited solely by the appended claims.

What is claimed is:

1. A method for contactless, real-time, in-situ monitoring of a chemical etching process during etching of at least one wafer in a wet chemical etchant bath, said method comprising the steps of:

a) providing two conductive electrodes in the wet chemical bath, wherein said two electrodes are proximate to but not in contact with the at least one wafer and further wherein each of the electrodes is positioned on an opposite side of the at least one wafer;

b) monitoring an electrical characteristic between the two electrodes as a function of time in the etchant bath of the at least one wafer, wherein a prescribed change in the electrical characteristic is indicative of a prescribed condition of the etching process; and c) recording a plurality of values of said electrical characteristic as a function of time during etching.

2. The method of claim 1, wherein the monitoring of an electrical characteristic in step (b) comprises monitoring impedance and further wherein the prescribed change in the electrical characteristic comprises a prescribed change in impedance.

3. The method of claim 2, wherein the monitoring of an electrical characteristic in step (b) comprises monitoring impedance and further wherein the prescribed change in the electrical characteristic comprises a prescribed change in a component of impedance, wherein said component is selected from the group consisting of admittance, reactance, resistance, capacitance, and inductance.

4. The method of claim 1, wherein an instantaneous etch rate is determined in real time from at least two of the recorded plurality of values.

5. The method of claim 4, further comprising the step of controlling the etching process in response to the instantaneous etch rate, wherein the instantaneous etch rate is determined in real time.

6. The method of claim 1, wherein an average etch rate is determined in real time from at least two of the recorded plurality of values.

7. The method of claim 6, further comprising the step of controlling the etching process in response to the average etch rate, wherein the average etch rate is determined in real time.

8. The method of claim 1, wherein an etching end point is determined in real time from at least two of the recorded plurality of values.

9. The method of claim 8, further comprising the step of controlling the etching process in response to the etching end point, wherein the end point is determined in real time.

10. A method for contactless, real-time, in-situ monitoring of a chemical etching process during etching of at least one wafer in a wet chemical etchant bath, said method comprising the steps of:

a) providing two conductive electrodes in the wet chemical bath, wherein said two electrodes are proximate to but not in contact with the at least one wafer;

b) monitoring an impedance between the two electrodes as a function of time in the etchant bath of the at least one wafer, wherein a prescribed change in the impedance is indicative of a prescribed condition of the etching process; and c) recording a plurality of values of said electrical characteristic as a function of time during etching.

11. A method for contactless, real-time, in-situ monitoring of a chemical etching process during etching of at least one wafer in a wet chemical etchant bath, said method comprising the steps of:

a) providing two conductive electrodes in the wet chemical bath, wherein said two electrodes are proximate to but not in contact with the at least one wafer and further wherein each of the electrodes is positioned on an opposite side of the at least one wafer;

b) monitoring an impedance between the two electrodes as a function of time in the etchant bath of the at least one wafer, wherein a prescribed change in the impedance is indicative of a prescribed condition of the etching process; and c) recording a plurality of values of said electrical characteristic as a function of time during etching.

* * * * *